United States Patent [19]

Ondetti et al.

[11] 4,151,172
[45] Apr. 24, 1979

[54] PHOSPHONOACYL PROLINES AND RELATED COMPOUNDS

[75] Inventors: Miguel A. Ondetti, Princeton; Edward W. Petrillo, Pennington, both of N.J.

[73] Assignee: E. R. Squibb & Sons, Inc., Princeton, N.J.

[21] Appl. No.: 926,177

[22] Filed: Jul. 20, 1978

Related U.S. Application Data

[63] Continuation-in-part of Ser. No. 823,818, Aug. 11, 1977, abandoned.

[51] Int. Cl.$^2$ ............................................. C07D 207/16
[52] U.S. Cl. ............................ 260/326.2; 260/326.47; 424/274
[58] Field of Search .................... 260/326.2, 326.47

[56] References Cited

U.S. PATENT DOCUMENTS

| 4,025,332 | 5/1977 | Franz ........................................ 71/86 |
| 4,046,889 | 9/1977 | Ondetti et al. ...................... 260/326.2 |
| 4,048,156 | 9/1977 | Langesdorf, Jr. ................. 260/326.2 |

OTHER PUBLICATIONS

Swyryd et al.; J. Biol. Chem., vol. 249, p. 6945 (1974).

Klee et al.; Chem. Abs., vol. 58: 3503h (1962).

*Primary Examiner*—Donald G. Daus
*Assistant Examiner*—Mary Lee
*Attorney, Agent, or Firm*—Lawrence S. Levinson; Merle J. Smith

[57] ABSTRACT

New phosphonoacyl prolines and related compounds have the general formula

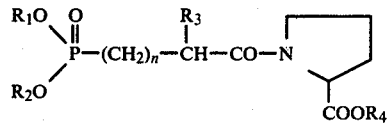

wherein
 $R_1$ and $R_2$ each is hydrogen, lower alkyl, lower alkenyl, unsustituted or substituted phenyl-lower alkyl, or a metal ion;
 $R_3$ is hydrogen or lower alkyl;
 $R_4$ is hydrogen, lower alkyl, phenyl-lower alkyl or a metal ion; and
 n is 0 or 1.

These compounds are useful as hypotensive agents.

19 Claims, No Drawings

PHOSPHONOACYL PROLINES AND RELATED COMPOUNDS

This application is a continuation-in-part of application Ser. No. 823,818, filed Aug. 11, 1977, now abandoned.

SUMMARY OF THE INVENTION

This invention relates to new phosphonoacyl prolines and related compounds which have the formula

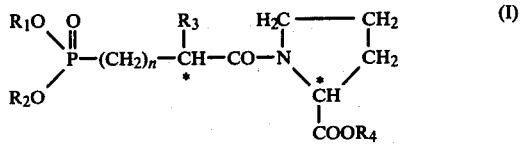

$R_1$ and $R_2$ each is hydrogen, lower alkyl, lower alkenyl, unsubstituted or substituted phenyl-lower alkyl or a metal ion;
$R_3$ is hydrogen or lower alkyl;
$R_4$ is hydrogen, lower alkyl, phenyl-lower alkyl or a metal ion; and
n is 0 or 1.

DETAILED DESCRIPTION OF THE INVENTION

In formula I, the lower alkyl groups represented by the symbols are straight or branched chain aliphatic hydrocarbon groups having up to seven carbon atoms, for example, methyl, ethyl, propyl, isopropyl, butyl, sec.butyl, t-butyl and the like. The $C_1$–$C_4$ members and especially the $C_1$–$C_2$ members are preferred. The phenyl-lower alkyl groups are aralkyl radicals of the same type, phenylmethyl and phenylethyl being especially preferred. The phenyl substituent of these groups can also be mono substituted, bearing a nitro, halo or lower alkyl group preferably in the 4-position. The nitrophenyl-lower alkyl groups are aralkyl radicals of the same type, (4-nitrophenyl)methyl being especially preferred. The four common halogens are contemplated by the term halo, chlorine and bromine being preferred.

The lower alkenyl groups are similar monounsaturated, straight or branched chain aliphatic hydrocarbon groups having up to seven carbon atoms. Those having up to four carbons are preferred, especially allyl.

The metal ions represented by $R_1$, $R_2$ and $R_4$ are monovalent metal ions, preferably the alkali metal ions, especially sodium, potassium and lithium.

Preferred embodiments of this invention are those compounds of formula I wherein n is 0 or 1, especially 0; $R_1$ and $R_2$ each is hydrogen, lower alkyl, especially methyl or ethyl, or alkali metal, especially lithium; $R_3$ is hydrogen or lower alkyl, especially methyl; and $R_4$ is hydrogen or alkali metal, especially lithium. Compounds in which at least one of the groups $R_1$ and $R_2$ is hydrogen are especially preferred.

The compounds of this invention are produced by reacting proline, preferably in the form of a lower alkyl or phenyl-lower alkyl ester in which the ester group is easily removed, e.g., the t-butyl ester, phenylmethyl ester or the like, with a phosphonoacetic acid or phosphonopropionic acid of the formula

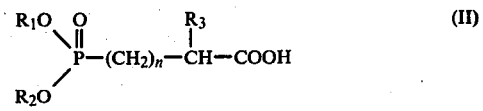

in the presence of a condensing agent like 1,1'-carbonyldiimidazole or dicyclohexylcarbodiimide and in an inert organic solvent like acetonitrile, dichloromethane, ether, tetrahydrofuran, dioxane or the like.

When $R_1$ and/or $R_2$ is phenylmethyl, 2-propenyl, or (4-nitrophenyl)methyl or $R_4$ is phenylmethyl, for example, these can be converted to hydrogen by catalytic reduction, e.g., with palladium on carbon or palladium on barium sulfate according to conventional methods.

When $R_4$ is an easily removable ester group like t-butyl, treatment of the ester with trifluoroacetic acid and anisole yields the free acid, i.e., $R_4$ is hydrogen.

The acids form metal salts like alkali metal salts by treatment with a metal hydroxide, e.g., in aqueous solution, according to conventional methods.

The proline esters are produced by any of a variety of known esterification methods utilizing a lower alkanol, or phenyl-lower alkanol $R_4$—OH (particularly in peptide syntheses) as illustrated in U.S. Pat. No. 4,046,889, Sept. 6, 1977; J. Org. Chem. 28, 176(1963); Pettit, *Synthetic Peptides*, Vol. 3 (Academic Press, 1975), pages 17 to 24; Bodanszky et al., *Peptide Synthesis*, 2nd ed. (Wiley & Sons, 1976), pages 49 to 56; Greenstein et al., *Chemistry of the Amino Acids*, Vol. 2 (Wiley & Sons, 1961), page 782 et seq.; J. Chromatog 44, 269 (1969); and sources cited therein. Preferred are those compounds wherein the proline portion of the molecule is in the L-form. When $R_3$ is other than hydrogen, the carbon atom to which it is attached is asymmetric so that stereoisomeric or racemic mixtures thereof occur. Here also the L-isomeric form is preferred.

The starting materials of formula II can be produced by various methods. For example, when $R_1$ and $R_2$ are lower alkyl, lower alkenyl or phenyl-lower alkyl other than phenylmethyl, compounds of formula II can be made by reacting tris(2-propenyl)phosphite with a bromo ester of the formula

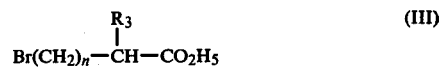

wherein $R_5$ is lower alkyl, preferably methyl or ethyl, to obtain a compound of the formula

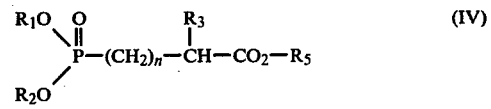

and saponifying the compound of formula IV with alkali to obtain the compound of formula II.

Compounds of formula II wherein $R_1$ and $R_2$ are phenylmethyl are produced by hydrolyzing a compound of formula IV, e.g., with boiling aqueous hydrochloric acid, to obtain a compound of formula IV wherein $R_1$, $R_2$ and $R_5$ each is hydrogen. The compound so obtained is reacted with methanol and hydrochloric acid to yield a compound of formula IV wherein $R_1$ and $R_2$ are both hydrogen and $R_5$ is methyl. The compound so obtained is reacted with an agent such as 1-phenylmethyl-3-p-tolyltriazene or α-diazotoluene to obtain a compound of formula IV wherein $R_1$ and $R_2$ are phenylmethyl and $R_5$ is methyl. The compound so obtained is converted to a compound of formula II as described above.

Compounds of formula II wherein $R_2$ is phenylmethyl and $R_1$ is lower alkyl, lower alkenyl or phenyl-lower alkyl other than phenylmethyl are obtained by reacting a compound of formula IV, wherein $R_1$ and $R_2$ are lower alkyl, lower alkenyl or phenyl-lower alkyl with phosphorus pentachloride to obtain a compound of the formula

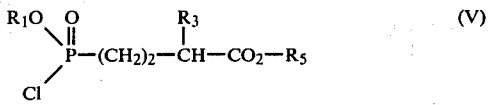

(V)

which is then reacted with benzyl alcohol in the presence of a base such as triethylamine or the like to obtain a compound of formula IV wherein $R_1$ is lower alkyl, lower alkenyl or phenyl-lower alkyl and $R_2$ is phenylmethyl. The compound so obtained is converted to a compound of formula II as described above.

Compounds of formula II wherein $R_1$ is lower alkyl, phenyl-lower alkyl, substituted phenyl-lower alkyl, or lower alkenyl and $R_2$ is lower alkyl, phenyl-lower alkyl, substituted phenyl lower alkyl or lower alkenyl, different from $R_1$, can be made by reacting a compound of formula IV, wherein $R_1$ and $R_2$ are lower alkyl, with phosphorus pentachloride to obtain a compound of the formula

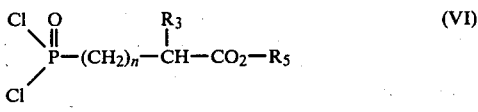

(VI)

The compound so obtained is reacted successively with alcohols of the formula $R_1$—OH and $R_2$—OH in the presence of a base such as triethylamine, dimethylaniline or the like to obtain a compound of formula IV wherein $R_1$ is lower alkyl, phenyl-lower alkyl, substituted phenyl-lower alkyl or lower alkenyl and $R_2$ is lower alkyl, phenyl-lower alkyl, substituted phenyl-lower alkyl or lower alkenyl, different from $R_1$. The compound so obtained is converted to a compound of formula II as described above.

Additional experimental details are provided in the illustrative examples which follow below.

The compounds of this invention are angiotensin converting enzyme inhibitors and are useful as hypotensive agents, particularly for the reduction of angiotensin dependent hypertension. By administering a composition containing one or a combination of angiotensin converting enzyme inhibitors of this invention to a hypertensive mammal, it intervenes in the renin→angiotensinogen→angiotensin I→angiotensin II sequence and the hypertension is reduced or alleviated.

A single dose, or preferably two to four divided daily doses, provided on a basis of 30 to 300 mg. per kilogram per day and especially about 10 to 100 mg. per kilogram per day is appropriate to bring about a reduction in elevated blood pressure. The animal model experiments described by Engel., Proc. Soc. Exp. Biol. Med. 143, 483 (1973) provide a valuable guide.

The composition is preferably administered subcutaneously, intramuscularly, intravenously or intraperitoneally, but it can also be administered orally with a dose of 10–1000 mg. per kilogram per day. The compound or compounds of formula I can be formulated as tablets, capsules or elixirs for oral administration. Sterile solutions or suspensions can be used for parenteral use.

About 100 to 500 mg. of a compound or compounds of formula I can be compounded with a physiologically acceptable vehicle, carrier, excipient, binder, preservative, stabilizer, flavor, etc., in a conventional unit dosage form as called for by accepted pharmaceutical practice. The amount of active substance is selected so as to provide a dosage in the range indicated.

The following examples are illustrative of the invention and represent preferred embodiments. All temperatures are in degrees Celsius.

EXAMPLE 1

1-(Phosphonoacetyl)-L-Proline (a) [Bis(2-propenyloxy)phosphinyl]Acetic Acid, Methyl Ester Triallyl phosphite (20.2 g., 0.01 mol.) and methyl bromoacetate (14.4 g., 0.01 mol.) are combined and heated at 110° under a slow stream of nitrogen for 2.5 hours. The mixture is then distilled and the fraction with b.p. 95°–102°/0.05mm is collected to obtain a total of 9.0 g. (38%) of [bis(2-propenyloxy)phosphinyl]acetic acid, methyl ester.

(b) [Bis(2-propenyloxy)phosphinyl]Acetic Acid

The ester obtained in part a (9.0 g., 0.038 mol.) is dissolved in 40 ml. of 1N potassium hydroxide and let stand overnight. The mixture is extracted with ether, then the aqueous layer is acidified and extracted with ethyl acetate. The acidic extracts are washed with brine, dried (MgSO$_4$) and evaporated in vacuo to a viscous liquid. The [bis(2-propenyloxy)phosphinyl]acetic acid weights 7.1 g. (85%).

(c) [Bis(2-propenyloxy)phosphinyl]Acetyl-L-Proline, tert-Butyl Ester

[Bis(2-propenyloxy)phosphinyl]acetic acid (7.0 g., 0.032 mol.) is dissolved in 200 ml. of acetonitrile and stirred in an ice bath under a drying tube. 1,1′-Carbonyldiimidazole (5.5 g., 0.032 mol.) is then added and the mixture is stirred for 45 minutes. L-Proline t-butyl ester (5.5 g., 0.032 mol.) is then added, the ice bath removed, and the mixture stirred overnight. The solution is then evaporated in vacuo and the residue taken up in ethyl acetate and washed with 5% potassium bisulfate, saturated sodium bicarbonate, and brine, then dried (MgSO$_4$) and evaporated to a viscous liquid (10.7 g., 89%). The product [Bis(2-propenyloxy)phosphinyl]acetyl-L-proline, tert-butyl ester is substantially pure by tlc ($R_f$=0.35, silica gel, ethyl acetate; several trace impurities).

(d) 1-(Phosphonoacetyl)-L-Proline, tert-Butyl Ester

A suspension of 5% palladium on barium sulfate catalyst (200 mg.) in 75 ml. of water and 75 ml. of acetic acid is equilibrated with hydrogen at atmospheric pressure. The proline ester from part c (10.7 g., 0.028 mol.) in 150 ml. of methanol is added and the mixture is hydrogenated overnight. The total change in gas volume is −700 ml. The mixture is filtered through Celite and the filtrate evaporated in vacuo to a viscous residue. Trituration with ethyl acetate causes precipitation of a white solid which is filtered and washed with ethyl acetate, m.p. 130° (decomposition, vigorous foaming). The product, 1-(phosphonoacetyl)-L-proline, tert-butyl ester is homogeneous by tlc ($R_f$=0.45, silica gel, n-butanol/acetic acid/water 3:1:1); total yield 5.4 g. 64%.

(e) 1-(Phosphonoacetyl)-L-Proline

The tert-butyl ester from part d (1.2 g., 0.0041 mol.) is dissolved in 36 ml. of trifluoroacetic acid and 4 ml. of anisole and let stand for 1 hour. The solution is evaporated in vacuo, the residue is taken up in water and the aqueous solution is washed with ether. Two-thirds of the aqueous solution is then lyophilized, yielding 480 mg. (74%) of white solid, 1-(phosphonoacetyl)-L-proline, which is transferred into vials in a glove bag under nitrogen.

Anal. Calc'd. for $C_7H_{12}NO_6P$: C, 35.45; H, 5.10; N, 5.91; P, 13.06. Found: C, 35.84; H, 5.47; N, 6.14.

After drying to constant weight at 40°, Found: C, 38.11; H, 5.61; N, 6.81.

The substance cannot be dried completely without decomposition.

EXAMPLE 2

1-(Phosphonoacetyl)-L-Proline, Lithium Salt

A solution of 1.184 g. (0.005 mol.) of 1-(phosphonoacetyl)-L-proline in 90 ml. of redistilled water is adjusted to pH 9.2 by the addition of 148 ml. of 0.1 N lithium hydroxide. The resultant solution is filtered through a millipore filter and then lyophilized. The weight of lyophilizate, 1-(phosphonoacetyl)-L-proline, lithium salt is 1.219 g. (93%).

EXAMPLE 3

1-(1-Oxo-3-Phosphonopropyl)-L-Proline (a) 3-[Bis(2-propenyloxy)phosphinyl]Propionic Acid Methyl Ester Triallylphosphite (21 g., 0.01 mole) and methyl-3-bromopropionate (16.7 g., 0.01 mole) are stirred at 110° for six hours while a stream of nitrogen is bubbled through the reaction mixture. The mixture is then distilled to yield a main fraction comprising 3-[bis(2-propenyloxy)phosphinyl]propionic acid, methyl ester, b.p. 124°–30°/0.05 mm., yield 8.4 g. (44%).

(b) 3-[Bis(2-propenyloxy)phosphinyl]propionic Acid

The methyl ester from part a (4.2 g., 0.016 mole) is stirred with 18 ml. of potassium hydroxide for 18 hours. The solution is extracted with ether, and the aqueous layer is acidified with concentrated hydrochloric acid, saturated with sodium chloride and extracted with ethyl acetate. The acidic extracts are dried ($Na_2SO_4$) and evaporated in vacuo to a clear oil, 3-[bis(2-propenyloxy)phosphinyl]propionic acid, yield 3.4 g. (85%).

(c) 1-[3-[Bis(2-propenyloxy)phosphinyl]-1-Oxopropyl]-L-proline, tert-Butyl Ester 3-[bis(2-propenyloxy)phosphinyl]propionic acid (3.4 g., 0.014 mol.) is dissolved in 75 ml. of acetonitrile and stirred in an ice bath under a drying tube. 1,1'-Carbonyldiimidazole (2.26 g., 0.014 mole) in 25 ml. of acetonitrile is added and the mixture is stirred for 1 hour. L-Proline t-butyl ester (2.38 g., 0.014 mole) is added, the ice bath is removed, and the mixture is stirred overnight. The solution is evaporated in vacuo, the residue dissolved in ethyl acetate and washed with 5% potassium bisulfate, saturated sodium bicarbonate solution and brine, then dried ($Na_2SO_4$) and evaporated to a viscous liquid, 1-[3-[bis(2-propenyloxy)phosphinyl)]-1-oxopropyl]-L-proline, tert-butyl ester, yield 4.2 g., 77%.

(d) 1-(1-Oxo-3-Phosphonopropyl)-L-Proline, tert-Butyl Ester

A suspension of 5% palladium on barium sulfate catalyst (80 mg.) in 30 ml. of water and 30 ml. of acetic acid is equilibrated with hydrogen at atmospheric pressure. The proline ester from part c (3.0 g., 0.008 mol.) in 40 ml. of methanol is added and the mixture hydrogenated overnight. The total change in gas volume is 340 ml. The mixture is filtered through Celite and the filtrate evaporated in vacuo to a viscous oil. Trituration with ethyl acetate yields 460 mg. (19% yield) of crystalline 1-(1-oxo-3-phosphonopropyl)-L-proline, tert-butyl ester, m.p. 157°–158° (d).

(e) 1-(1-Oxo-3-Phosphonopropyl)-L-proline

The tert-butyl ester from part d (460 mg., 0.0015 mol.) is dissolved in 15 ml. of trifluoroacetic acid and 1.5 ml. of anisole and stirred for one hour at room temperature. The solution is evaporated in vacuo, the residue is taken up in water and washed with ether. The aqueous layer (18 ml.) is lyophilized to amorphous, white solid 1-(1-oxo-3-phosphonopropyl)-L-proline. Total yield 395 mg. (quantitative).

EXAMPLE 4

1-[(Ethoxyhydroxyphosphinyl)acetyl]-L-Proline (a) Ethyl(Chloroethoxyphosphinyl)acetate Ethyl(diethoxyphosphinyl)acetate (11.2 gm., 0.05 mol.) and phosphorus pentachloride (10.5 gm., 0.05 mol.) are dissolved in 200 ml. of benzene and refluxed overnight. The solvent is removed in vacuo, leaving yellow, oily, ethyl(ethoxychlorophosphinyl)acetate as residue (11.5 gm.).

(b) Ethyl[Ethoxy[(phenylmethyl)oxy]phosphinyl]Acetate

The oil from part a is taken up in 100 ml. of ether and added to an ice-cooled solution of triethylamine (7.7 ml., 0.055 mol.) and benzyl alcohol (6.0 ml., 0.056 mol.) in 100 ml. of ether. After stirring overnight, the mixture is washed with water, brine, dried ($MgSO_4$) and evaporated in vacuo. The resulting oil is distilled and a main fraction, b.p. 126°–140°/0.04 mm., comprising ethyl[ethoxy[(phenylmethyl)oxy]phosphinyl]acetate is collected, yield 7.0 gm. (49%).

(c) [Ethoxy[(Phenylmethyl)oxy]Phosphinyl]Acetic Acid

The ester from part b (5.0 gm., 0.0175 mol.) is stirred overnight with 19.2 ml. 1 N potassium hydroxide. The mixture is extracted with ether, acidified with concentrated hydrochloric acid, and extracted with ethyl acetate. The acidic extracts are washed with brine, dried ($Na_2SO_4$) and evaporated to an oil, [ethoxy[(phenylmethyl)oxy]phosphinyl]acetic acid (5.1 gm., 91%).

(d) [[Ethoxy[(Phenylmethyl)Oxy]Phosphinyl]Acetyl]-L-Proline phenylmethyl ester

L-Proline phenylmethyl ester hydrochloride (3.74 gm., 0.0155 mol.) is dissolved in 35 ml. of chloroform at 0° and treated with triethylamine (1.58 gm., 0.0155 mol.). Ether is then added and the resulting suspension is filtered. The filtrate is evaporated in vacuo to an oil (3.1 gm., 95%).

[Ethoxy[(phenylmethyl)oxy]phosphinyl]acetic acid (4.0 gm., 0.0155 mol.) is dissolved in 100 ml. acetonitrile at 0°. 1,1'-Carbonyldiimidazole (2.5 gm., 0.0155 mol.) is added and stirred for 1 hour. The above oil in 30 ml. acetonitrile is added and the mixture is stirred overnight at room temperature, then evaporated in vacuo. The residue is taken up in ethyl acetate, washed with 5% potassium bisulfate, saturated sodium bicarbonate and brine, dried ($Na_2SO_4$) and evaporated.

The residue is chromatographed on 250 gm. of silica gel using ethyl acetate/hexane - ethyl acetate. The main fraction ($R_f$=0.25, silica gel, ethyl acetate) amounts to 2.7 gm. (40%) of 1-[[ethoxy[(phenylmethyl)oxy]phosphinyl]acetyl]-L-proline, phenylmethyl ester.

(e) 1-[(Ethoxyhydroxyphosphinyl)Acetyl]-L-Proline

A suspension of 10% palladium on carbon catalyst (60 mg.) in 50 ml. methanol is equilibrated with hydrogen and the ester from part d (2.0 gm., 0.0045 mol.) in 100 ml. methanol is added and stirred 3 hours. Hydrogen uptake amounts to 195 ml. (0.0085 mol.). The mixture is filtered through Celite, the filtrate evaporated and the residue taken up in water. The solution is filtered through a millipore filter and lyophilized into vials, affording the product, 1-[(ethoxyhydroxyphosphinyl)acetyl]-L-proline, as an extremely hygroscopic white foam (0.9 gm., 75%).

EXAMPLE 5

1-[(Dimethoxyphosphinyl)Acetyl]-L-Proline (a) (Dimethoxyphosphinyl)Acetic Acid

Methyl(dimethoxyphosphinyl)acetate (18.2 g., 0.1 mole) and 1 N sodium hydroxide (100 ml., 0.1 mole) are combined and stirred at room temperature overnight. The reaction mixture is poured onto AG50W-X2 cation exchange resin (200 ml.) and eluted with double distilled water. The acidic fractions are combined and concentrated in vacuo. The residue is dissolved in dichloromethane, dried over magnesium sulfate and concentrated in vacuo to yield 16.8 g. of product, (dimethoxyphosphinyl)acetic acid, yield quantitative.

(b) 1-[(Dimethoxyphosphinyl)Acetyl]-L-Proline, Phenylmethyl Ester

A solution of (dimethoxyphosphinyl)acetic acid (6.72 g., 0.04 moles) and 1,1'-carboxyldiimidazole (6.49 g., 0.04 moles) in anhydrous acetonitrile (250 ml.) is stirred for one hour at 0°. A solution of L-proline phenylmethyl ester (8.16 g., 0.04 moles) in anhydrous acetonitrile (10 ml.) is added to the above solution and stirred one hour at 0°, then left at room temperature overnight. The reaction mixture is concentrated in vacuo. The residue is dissolved in ethyl acetate and washed with 5% potassium bisulfate and 5% sodium bicarbonate. The ethyl acetate layer is dried over sodium sulfate and concentrated in vacuo. The residue is chromatographed on silica gel (1000 ml.) eluting with (1) EtOAc (2) 2% MeOH/EtOAc and (3) 5% MeOH/EtOAc to yield 12 g. of 1-[(dimethoxyphosphinyl)acetyl]-L-proline, phenylmethyl ester. TLC: silica gel, 10% MeOH/EtOAc, $R_f=0.2$, UV visualization.

(c) 1-[(Dimethoxyphosphinyl)Acetyl]-L-Proline

A mixture of 1-[(dimethoxyphosphinyl)acetyl]-L-proline, phenylmethyl ester (3.55 g., 0.01 moles) and 10% Pd/C (350 mg.) in absolute ethanol (200 ml.) is stirred under one atmosphere of hydrogen until 225 ml. of hydrogen has been consumed. The reaction mixture is filtered and concentrated in vacuo. The residue is dissolved in double distilled water and filtered through AG50W-X2 cation exchange resin (20 ml.). The acidic fractions are combined, filtered through a millipore filter, and lyophilized to yield 2.3 g. of 1-[(dimethoxyphosphinyl)acetyl]-L-proline as a glass.

Anal. Calc'd. for $C_9H_{16}NO_6P$: C, 40.76; H, 6.08; N, 5.28; P, 11.69. Found: C, 41.02; H, 5.83; N, 5.57; P, 11.88.

EXAMPLE 6

1-(1-Oxo-2-Phosphonopropyl)-L-Proline (a) Ethyl 2-(Diethoxyphosphinyl)Propionate Triethylphosphite (83 g., 0.5 moles) is heated to 140° and treated dropwise over ninety minutes with ethyl 2-bromopropionate (90.5 g., 0.5 moles). As ethyl bromide distills off, the temperature is gradually raised to 160°. After the addition is complete, the temperature is raised to 190°. After heating the reaction mixture an additional forty-five minutes at 190°, the mixture is distilled in vacuo to yield 105 g. of ethyl-2-(diethoxyphosphinyl)propionate, b.p. 105°–110° C./2 mm.

(b) 2-Phosphonopropionic Acid

A mixture of ethyl-2-(diethoxyphosphinyl)propionate (15 g., 0.063 moles) in 6 N hydrochloric acid (150 ml.) is heated to reflux for 2.5 hours. After this time, the reaction vessel is fitted with a Dean-Stark trap and heated at reflux an additional thirty minutes. The reaction mixture is concentrated in vacuo to yield 2-phosphonopropionic acid (quantitative).

(c) Methyl 2-Phosphonopropionate

A solution of 2-phosphonopropionic acid (11.2 g., 0.073 moles) in methanol (150 ml.) is heated at reflux for eighteen hours. The methanol is removed in vacuo. Electrophoresis (0.1 N $NH_4HCO_3$, 2000 V, 20 minutes, 7.5 cm) indicates complete conversion to the desired product, methyl 2-phosphonopropionate; yield quantitative.

(d) Methyl 2-[Bis[(Phenylmethyl)Oxy]Phosphinyl]Propionate

A solution of 3-benzyl-1-p-tolyltriazene (12.38 g., 0.05 moles) in anhydrous ether (150 ml.) is chilled in an ice bath and treated with a solution of methyl 2-phosphonopropionate (4.23 g., 0.025 moles) in ethyl acetate (5 ml.). After the addition, the reaction is stirred at room temperature for four hours. The mixture is then washed with 10% hydrochloric acid, water, and brine, dried over sodium sulfate, and concentrated in vacuo. The resultant red oil is chromatographed on silica gel (500 ml.) eluting with (1) 10% EtOAc/hexane (1 liter) (2) 30% EtOAc/hexane (1 liter) and (3) 50% EtOAc/hexane (1 liter) to yield 2.8 g. of product methyl 2-[bis[phenylmethyl)oxy[phosphinyl)]propionate. TLC (silica gel; hexane/ethyl acetate (1:1); $R_f=0.2$, UV visualization).

(e) 2-[Bis[(Phenylmethyl)Oxy]Phosphinyl]Propionic Acid

A solution of methyl 2-[bis[(phenylmethyl)oxy]phosphinyl]-propionate (2.73 g., 0.008 moles) and 1 N sodium hydroxide (8.1 ml., 0.008 moles) in methanol is stirred at room temperature for three days. The reaction mixture is concentrated in vacuo. The residue is dissolved in water and washed with diethyl ether. The aqueous layer is acidified with 5% potassium bisulfate and extracted several times with ethyl acetate. The combined ethyl acetate extracts are dried over sodium sulfate and concentrated in vacuo to yield 2.7 g. of product, 2-[bis[(phenylmethyl)oxy]phosphinyl]propionic acid (silica gel; benzene/acetic acid (7:1); $R_f=0.3$; UV visualization).

(f) 1-[2-[Bis[(Phenylmethyl)Oxy]Phosphinyl]Propionyl]-L-Proline, Phenylmethyl Ester A solution of 2-[bis[(phenylmethyl)oxy]phosphinyl]-propionic acid (2.47 g., 0.076 moles) and 1,1'-carbonyldiimidazole (1.24 g. 0.076 moles) in dry acetonitrile (100 ml.) is stirred at 0° for one hour. A solution of L-proline, phenylmethyl ester (1.56 g., 0.076 moles) in acetonitrile (5 ml.) is then added and the reaction is stirred one hour at 0°, then left at room temperature overnight. The reaction mixture is concentrated in vacuo. The residue is dissolved in ethyl acetate and washed with 5% potassium bisulfate and 5% sodium bicarbonate. The ethyl acetate solution is dried over sodium sulfate and concentrated in vacuo. The residue is chromatographed on silica gel (500 ml.) eluting with (1) 10% EtOAc/hexane (2) 25% EtOAc/hexane and (3) EtOAc to yield 3.8 g. of product, 1-[2-[bis[(phenylmethyl)oxy]phosphinyl]propionyl]-L-proline, phenylmethyl ester, a mixture of the two diastereomers. TLC (silica gel; ethyl acetate; $R_f=0.35$ and 0.40; UV visualization).

(g) 1-(1-Oxo-2-Phosphonopropyl)-L-Proline

A mixture of 1-[2-[bis[(phenylmethyl)oxy]phosphinyl]propionyl]-L-proline; phenylmethyl ester (3.48 g., 0.067 moles) and 10% Pd/C (350 mg.) in absolute ethanol (250 ml.) is stirred under one atmosphere of hydrogen until 450 ml. of hydrogen has been consumed. The reaction mixture is filtered and concentrated in vacuo. Electrophoresis (0.1 N $NH_4HCO_3$, 2000 V, 15 minutes, 10.5 cm) indicates only one product. The residue is dissolved in double distilled water and filtered through a millipore filter. A portion of the filtrate is lyophilized to yield 960 mg. of 1-(1-oxo-2-phosphonopropyl)-L-proline, an extremely hygroscopic substance.

Anal. Calc'd. for $C_8H_{14}NO_6P$: C, 38.25; H, 5.62; N, 5.62; P, 12.33.

Anal. Calc'd. for $C_8H_{14}NO_6P\cdot0.35H_2O$: C, 37.32; H, 5.75, N, 5.44; P, 11.99. Found: C, 37.67; H, 5.66, N, 5.32; P, 11.66.

EXAMPLE 7

1-(1-Oxo-2-Phosphonopropyl)-L-Proline, Trilithium Salt

A solution of 1-(1-oxo-2-phosphonopropyl)-L-proline in double-distilled water (pH=1.6) is treated dropwise with a 1 M lithium hydroxide solution until the pH reaches 9.2. The solution is then filtered through a millipore filter and lyophilized to yield 640 mg. of 1-(1-oxo-2-phosphonopropyl)-L-proline, trilithium salt, m.p.>330°.

Anal. Calc'd. for $C_8H_{11}NO_6P\cdot3Li$: C, 35.72; H, 4.12; N, 5.21; P, 11.52; Li, 7.74.

Anal. Calc'd. for $C_8H_{11}NO_6P\cdot3Li\cdot\frac{3}{4}H_2O$: C, 34.02; H, 4.46; N, 4.96; P, 10.96; Li, 7.37. Found: C, 34.24; H, 4.63; N, 5.00; P, 10.60; Li, 7.28.

EXAMPLE 8

1-[[Hydroxy[(2-Phenylethyl)Oxy]Phosphinyl]Acetyl]-L-Proline (a) (Dichlorophosphinyl)Acetic Acid, Methyl Ester Methyl(dimethoxyphosphinyl)acetate (36.4 gm., 0.2 mol.) is treated with phosphorus pentachloride (83.2 gm., 0.4 mol.). An exothermic reaction raises the temperature of the mixture to 80°. The reaction mixture is maintained at 80° for one hour, then distilled in vacuo to obtain 13.5 gm. of (dichlorophosphinyl)acetic acid, methyl ester, b.p. 95°–100°/1.5 mm.

(b) [[[(4-Nitrophenyl)methyl]Oxy][(2-phenylethyl)Oxy]Phosphinyl]-Acetic Acid, Methyl Ester (Dichlorophosphinyl)acetic acid, methyl ester (7.2 gm., 0.038 mol.) is stirred in 100 ml. of dichloromethane at 0° while 2-phenylethanol (4.6 gm., 0.038 mol.) and triethylamine (5.2 ml., 0.038 mol.) in 50 ml. of dichloromethane are added over 45 minutes. After stirring 2 hours, (4-nitrophenyl)methanol (5.8 gm., 0.038 mol.) and triethylamine in 50 ml. of dichloromethane are added and stirred overnight. The mixture is washed with water, saturated sodium bicarbonate and brine, and the organic layer is dried ($MgSO_4$) and evaporated to 10 gm. of brown oil. Chromatography on silica gel (1000 ml.) with dichloromethane-ethyl acetate yields 4.48 gm. of product, [[[(4-nitrophenyl)methyl]oxy][(2-phenylethyl)oxy]phosphinyl]acetic acid, methyl ester, as a viscous glass.

(c) [[[(4-Nitrophenyl)methyl]Oxy][(2-Phenylethyl)Oxy]-Phosphinyl]Acetic Acid

The phosphinyl acetic acid ester obtained in part b (4.48 gm., 0.011 mol.) is stirred with 1 N sodium hydroxide (12 ml.) overnight. The mixture is extracted with ether and the aqueous layer acidified, then extracted with dichloromethane. The dichloromethane extracts are dried ($Na_2SO_4$) and evaporated to 3.6 gm. of viscous oil. Chromatography on 300 ml. silica gel with acetic acid/benzene (1:10) yields 3.0 gm. of product, [[[(4-nitrophenyl)methyl]oxy][(2-phenylethyl)oxy]phosphinyl]-acetic acid as a viscous glass.

(d) 1-[[[[(4-Nitrophenyl)methyl]oxy][(2-Phenylethyl)Oxy]Phosphinyl]Acetyl]-L-Proline, Phenylmethyl Ester The phosphinyl acetic acid obtained in part c (2.65 gm., 0.007 mol.) and 1,1'-carbonyldiimidazole (1.14 gm., 0.007 mol.) are combined in 125 ml. of acetonitrile at 0° and stirred for 1 hour. L-proline phenylmethyl ester (1.44 gm., 0.007 mol.) is added and the mixture is stirred overnight at room temperature. The reaction mixture is concentrated in vacuo and partitioned between ethyl acetate and water. The ethyl acetate layer is washed with 5% potassium bisulfate and saturated sodium bicarbonate, then dried ($Na_2SO_4$) and evaporated to an oil. Chromatography on 300 ml. silica gel with acetic acid/benzene (1:11) yields 3.1 gm. of the desired product, 1-[[[[(4-nitrophenyl)methyl]-oxy][(2-phenylethyl)oxy]phosphinyl]acetyl]-L-proline, phenylmethyl ester, as a viscous glass.

(e) 1-[[[Hydroxy[(2-Phenylethyl)Oxy]Phosphinyl]Acetyl]-L-Proline

The proline ester from part d is substituted for the 1-[[ethoxy[(phenylmethyl)oxy]phosphinyl]acetyl]-L-proline phenylmethyl ester in the procedure of part e, Example 4, to obtain 1-[[hydroxy[(2-phenylethyl)oxy]phosphinyl]acetyl]-L-proline.

EXAMPLE 9

1-(Phosphonoacetyl)-1-Proline, Sodium Salt 0.1 N sodium hydroxide is substituted for the 0.1 N lithium hydroxide in the procedure of Example 2 to obtain 1-(phosphonoacetyl)-L-proline, sodium salt.

What is claimed is:

1. A compound of the formula $$\underset{R_2O}{\overset{R_1O}{\diagdown}}\overset{O}{\underset{\diagup}{\overset{\|}{P}}}-(CH_2)_n-\underset{R_3}{\overset{|}{C}H}-CO-N\underset{CH}{\overset{H_2C-CH_2}{\diagup}}\overset{}{\underset{|}{\underset{COOR_4}{|}}}$$

wherein $R_1$ and $R_2$ each is hydrogen, alkali metal ion, lower alkyl, lower alkenyl, phenyl-lower alkyl or monosubstituted phenyl-lower alkyl wherein the phenyl substituent is nitro, halo or lower alkyl;

$R_3$ is hydrogen or lower alkyl;

$R_4$ is hydrogen, lower alkyl, phenyl-lower alkyl or alkali metal ion; and n is 0 or 1.

2. The L-form of a compound of claim 1.

3. A compound as in claim 2 wherein $R_4$ is hydrogen.

4. A compound as in claim 2 wherein n is 0.

5. A compound as in claim 2 wherein n is 1.

6. A compound as in claim 1 wherein $R_1$, $R_2$ and $R_4$ each is hydrogen.

7. A compound as in claim 1 wherein $R_1$, $R_2$ and $R_4$ each is alkali metal.

8. A compound as in claim 1 wherein n is 0 or 1; $R_1$ and $R_2$ each is hydrogen, lower alkyl or alkali metal; and $R_3$ is hydrogen or lower alkyl and $R_4$ is hydrogen or alkali metal.

9. A compound as in claim 8 wherein the alkali metal group is lithium.

10. A compound as in claim 4 wherein $R_1$, $R_2$, $R_3$ and $R_4$ each is hydrogen.

11. A compound as in claim 4 wherein $R_1$, $R_2$ and $R_4$ each is lithium and $R_3$ is hydrogen.

12. A compound as in claim 5 wherein $R_1$, $R_2$, $R_3$ and $R_4$ each is hydrogen.

13. A compound as in claim 4 wherein $R_1$ is ethyl and $R_2$, $R_3$ and $R_4$ each is hydrogen.

14. A compound as in claim 4 wherein $R_1$, $R_2$ and $R_4$ each is hydrogen and $R_3$ is methyl.

15. The lithium salt of the compound of claim 14.

16. A compound as in claim 4 wherein $R_1$ and $R_2$ each is methyl and $R_3$ and $R_4$ each is hydrogen.

17. A compound as in claim 4 wherein $R_1$, $R_3$ and $R_4$ each is hydrogen and $R_2$ is phenylethyl.

18. A compound as in claim 1 wherein $R_1$ is nitrophenylmethyl.

19. A compound as in claim 4 wherein $R_1$ is (4-nitrophenyl)methyl, $R_2$ is (2-phenylethyl), $R_3$ is hydrogen and $R_4$ is phenylmethyl.

* * * * *